(12) United States Patent
Arnold et al.

(10) Patent No.: US 6,383,976 B1
(45) Date of Patent: May 7, 2002

(54) MULTIMETAL OXIDE MATERIAL FOR GAS-PHASE CATALYTIC OXIDATION OF ORGANIC COMPOUNDS

(75) Inventors: Heiko Arnold, Mannheim; Klaus Harth, Altleiningen; Hans-Peter Neumann, Ludwigshafen; Ulrich Hammon, Mannheim; Raimund Felder, Neustadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/452,452

(22) Filed: Dec. 2, 1999

(30) Foreign Application Priority Data

Dec. 3, 1998 (DE) .......................... 198 55 913

(51) Int. Cl.$^7$ ................................ B01J 23/00
(52) U.S. Cl. ................... 502/311; 502/315; 502/316; 502/317; 502/321; 502/322; 423/606
(58) Field of Search ................. 502/313, 315, 502/314, 335, 317, 316, 330, 321, 322, 332, 323, 325, 336, 337, 338; 423/606

(56) References Cited

U.S. PATENT DOCUMENTS

| | | | |
|---|---|---|---|
| 4,129,600 A | | 12/1978 | Childress et al. |
| 4,166,808 A | | 9/1979 | Daumas et al. |
| 5,144,090 A | * | 9/1992 | Honda et al. ............ 568/476 |
| 5,245,083 A | * | 9/1993 | Matsuura ............ 568/479 |
| 5,250,485 A | * | 10/1993 | Kuroda et al. ............ 502/159 |
| 5,663,113 A | * | 9/1997 | Midorikawa et al. ....... 502/314 |

FOREIGN PATENT DOCUMENTS

| | | |
|---|---|---|
| DE | 24 31 511 | 7/1974 |
| DE | 112 251 | 4/1975 |
| FR | 2 364 061 | 4/1978 |

* cited by examiner

*Primary Examiner*—Steven P. Griffin
*Assistant Examiner*—Edward M. Johnson
(74) *Attorney, Agent, or Firm*—Oblon, Spivak, McClelland, Maier & Neustadt, P.C.

(57) ABSTRACT

The multimetal oxide materials essentially consisting of $$Mo_{12}Bi_aX^1_bFe_cX^2_dX^3_eO_y \qquad (I)$$

where:
  $X^1$ is Co and/or Ni,
  $X^2$ is Si and/or Al,
  $X^3$ is an alkali metal,
  $0.3 \leq a \leq 1$,
  $2 \leq b \leq 10$,
  $0.5 \leq c \leq 10$,
  $0 \leq d \leq 10$,
  $0 \leq e \leq 0.5$ and
  y is the absolute value of the number which, assuming charge neutrality, is obtained from the sum of the valences and the stoichiometric coefficients of the other elements, the crystalline fractions containing, in addition to $\beta$-$X^1MoO_4$ as the main component, $Fe_2(MoO_4)_3$ as a secondary component and no $MoO_3$.

13 Claims, No Drawings

MULTIMETAL OXIDE MATERIAL FOR GAS-PHASE CATALYTIC OXIDATION OF ORGANIC COMPOUNDS

The present invention relates to multimetal oxide materials essentially of the formula $$Mo_{12}Bi_aX^1_bFe_cX^2_dX^3_eO_y \quad (I),$$

where

X$^1$ is Co and/or Ni, preferably Co,

X$^2$ is Si and/or Al, preferably Si,

X$^3$ is an alkali metal, preferably K, Na, Cs and/or Rb, in particular K, $0.3 \leq a \leq 1$, $2 \leq b \leq 10$, $0.5 \leq c \leq 10$, $0 \leq d \leq 10$, $0 \leq e \leq 0.5$ and y is the absolute value of the number which is obtained, assuming charge neutrality, from the valences and the stoichiometric coefficients of the other elements, the crystalline fractions containing, in addition to β-(Co or Ni)MoO$_4$ as the main component, Fe$_2$(MoO$_4$)$_3$ as a secondary component and no MoO$_3$. The present invention furthermore relates to the preparation of the multimetal oxide materials, moldings produced therefrom and the use of the multimetal oxide materials and of the moldings.

The expression "essentially" preferably means a content of at least 95, particularly preferably at least 99, % by weight. In particular, no other components are present.

Similar multimetal oxide materials are disclosed in EP-A 0 000 835. According to this publication, these multimetal oxide materials are formed by preforming, in the absence of the other constituents, the bismuth-molybdenum mixed oxide forming the catalytic key phase of these multimetal oxide materials, mixing said mixed oxides with sources of the other constituents of the multimetal oxide materials after its pre-formation and calcining the mixture after drying.

EP-B 0 575 897 discloses multimetal oxide materials which have three-demensional regions having the chemical composition Bi$_2$W$_2$O$_9$ with a maximum diameter of from 1 to 25 μm. These regions are delimited from their local environment owing to their chemical composition. The known materials are formed by means of a process in which first a finely divided powder comprising calcined mixed oxide is initially taken and the sources of the other components of the multimetal oxide materials are then added.

Both above-mentioned multimetal oxide materials are used for the gas-phase catalytic oxidation of organic compounds. Apart from their time-consuming and labor-intensive preparation, the known catalytic multimetal oxide materials are furthermore not completely satisfactory with respect to their selectivity.

EP-A-0 493 274 and DE-A-27 41 132 as well as DE-A-31 14 709 describe the preparation of multimetal oxide materials by precipitation, a mixed metal salt solution of the starting metals being precipitated with ammonium molybdate solution. The activity and selectivity of the catalysts obtained are not adequate for all applications.

It is an object of the present invention to provide multimetal oxide materials and a process for their preparation which do not have the above-mentioned disadvantages. In particular, the preparation is to be simplified; moreover, the multimetal oxide materials are to be improved with respect to their activity and selectivity in the gas-phase oxidation and are to permit a higher space-time yield.

This object is achieved by the multimetal oxide materials stated at the outset. The determination of the components is carried out by means of X-ray diffractometry.

Fe$_2$(MoO$_4$)$_3$ is present as a chiefly occurring secondary component. Preferably, Bi$_2$Mo$_3$O$_{12}$, X$^1_6$Mo$_{12}$Fe$_4$Bi$_{1.5}$O$_x$ or a mixture thereof is present as an additional component in the crystalline fractions, x having the meaning stated for y.

Preferably, no Bi$_3$FeMo$_2$O$_{12}$ is present in the crystalline fractions.

X$^1$ may be Co and/or Ni. Mixtures having a predominant proportion of Co are preferred; in particular, X$^1$ is Co.

The present invention also relates to a process for the preparation of such multimetal oxide materials, in which a) a first aqueous solution A of the constituents Bi, Fe and X$^1$ is prepared, b) a second aqueous solution B of the constituents Mo and X$^3$ is prepared, c) the solutions A and B are mixed, a solution or suspension of the constituent X$^2$ being mixed with the solution A, B or a mixture thereof, d) the mixture or precipitated product obtained in c) is dried and e) the product obtained in d) is calcined.

Preferably, the aqueous solutions A and B are mixed and the mixture thereof is mixed with a solution or suspension of the constituent X$^2$.

The calcination is preferably effected at from 450 to 490° C., in particular from 460 to 480° C., especially from 465 to 477° C.

The drying is preferably effected by means of spray drying.

It is preferable according to the invention if the multimetal oxide materials of the formula I are prepared by means of a one-pot process. Here, a first aqueous solution having the constituents Bi, Fe and X$^1$ is first prepared. The preparation of the first aqueous solution is effected from suitable water-soluble starting compounds of the constituents Bi, Fe and X$^1$. Such water-soluble compounds of said constituents are sulfates, halides, acetates, formates, nitrates, carbonates, etc. Among these water-soluble starting compounds, the nitrates are preferred for preparation of the first aqueous solution. To prepare the first aqueous solution, it may be necessary to dissolve the starting compounds at elevated temperatures, in particular at from 50 to 70° C.

A second aqueous solution B of the constituents Mo and X$^3$ is similarly prepared. In particular, ammonium molybdate is used for this purpose. The alkali metal X$^3$ is preferably potassium, which is used as KOH. This solution, too, can be prepared at from 50 to 70° C. The two solutions are then mixed, for example by pumping solution A into solution B. The constituent X$^2$ may be contained in solution A, solution B or the mixture or may be added to it in the form of a solution or suspension. Preferably, a silica sol is added to the mixture if X$^2$ is silicon in the mixture.

Mixing of the solutions results in precipitation of the metals.

If the catalytic multimetal oxide material is to have pores, it is preferable to use ammonium salts or nitrates as the starting compounds as feedstocks so that a pore-containing containing catalyst forms.

If no ammonium salts or nitrates are used, it is also possible to add ammonium nitrate, as a pore former, to one of the two aqueous solutions or to both aqueous solutions. If required, a finely divided suspension of alumina particles and/or silica particles can also be added to one or both abovementioned aqueous solutions. The alumina or the silica acts as an inert diluent.

After precipitation is complete, the precipitate is separated from the remainder of the solvent. For this purpose, it can be dried by evaporation. However, the separation is preferably effected by means of spray-drying. Spray-drying can be carried out by the cocurrent or countercurrent method. During the spray-drying, the temperature at the spray tower inlet is preferably about 400° C. and the temperature at the spray tower outlet from about 120 to 140° C. The spray-drying gives particles of the novel multimetal oxide material having a diameter of from about 1 to 100 μm. The powder obtained after the spray-drying is further processed depending on the desired catalyst formed. For the preparation of annular catalysts, the powder obtained is pelleted with the use of not more than 4% by weight of graphite (BET surface area 5–15 m²/g, mean particle diameter <30 μm) as a pelleting aid and is then decomposed at preferably from 150 to 300° C. for oxide formation. The resulting oxide material is then calcined at the abovementioned temperatures. The process step involving decomposition and that involving calcination can be carried out in an inert gas atmosphere, in air, under oxygen, nitrogen, etc. The calcination and the decomposition can be contiguous process steps. For the preparation of catalysts in chip form, the powder obtained after the spray-drying is kneaded, then dried and then coarsely milled. It is then decomposed and calcined as described and subsequently converted into chips and separated by sieving.

For the preparation of coated catalysts, the powder obtained after the spray-drying is kneaded, dried and coarsely milled and then decomposed as described. After the decomposition, milling to a defined particle size is effected, the catalyst carrier is coated and only thereafter is calcination effected.

The multimetal oxide material of the formula I $Mo_{12}Bi_aX^1_bFe_cX^2_dX^3_eO_y$, obtained by means of the novel process, contains Co and/or Ni, but preferably Co, as $X^1$. $X^2$ is Si and/or Al, preferably Si. $X^3$ comprises alkali metal elements Li, Na, K, Cs and/or Rb, preferably K, Na and/or Cs, particularly preferably K; the value of the variable a is from 0.3 to 1. Preferably, $0.4 \leq a \leq 0.1$, in particular $0.4 \leq a \leq 0.95$. The value of the variable b is from 2 to 10, preferably $4 \leq b \leq 8$, very particularly $6 \leq b \leq 8$; the value of the variable c is from 0.5 to 10, preferably from 1 to 5, in particular from 2 to 4. The value of the variable e is, according to the invention, from 0 to 0.5, in particular >0. Preferably, $0.01 \leq e \leq 0.5$, very particularly preferably $0.05 \leq e \leq 0.2$ The value for O (oxygen) is obtained from the absolute value of the sum of the valences and the stoichiometric coefficients of the other elements, i.e. of the cations. In the novel process, a multimetal oxide material in which the Co/Ni ratio is at least 2:1, preferably at least 3:1, particularly preferably at least 4:1, is preferably prepared. Very particularly preferably, only Co is present. The multimetal oxide material obtainable by means of the novel process is distinguished only by the overall composition of its components which is described above but also by a typical phase composition, as demonstrated in the Examples with reference to X-ray diffraction patterns.

In the case of particularly preferred novel multimetal oxide materials, the value for 1.5 (a+c)+b is from 11 to 14, preferably from 11.5 to 13, particularly preferably from 11.8 to 12.5. The limiting values are included in the stated ranges.

According to the invention, the novel multimetal oxide material is used for the preparation of moldings, in particular of catalyst moldings. For this purpose, it is used in the form of a powder. The shaping itself can be used before or after the calcination. Possible moldings are unsupported catalysts or coated catalysts. Coated catalysts prepared from the novel multimetal oxide material or annular unsupported catalysts, which can be obtained by pelleting or extrusion, are preferred. In addition, the catalyst may be present as chips.

In addition to the multimetal oxides, the catalyst may also contain further bismuth-containing oxides, such as $Bi_2W_2O_9$ or $Bi_2Mo_3O_{12}$. The oxides may be mixed in the form of a powder and processed to give catalysts.

The novel multimetal oxide materials are suitable for the selective gas-phase oxidation of organic compounds, in particular alkenes, such as propene. In particular, they are suitable for the preparation of α,β-unsaturated aldehydes and/or carboxylic acids from alkenes, alkanes, alkanones or alkenals. Particularly preferably, the novel multimetal oxide materials are used for the preparation of acrolein and acrylic acid from propene and methacrolein, respectively, and methacrylic acid from isobutene.

The Examples which follow illustrate the invention.

EXAMPLES

1. Preparation of the Active Component (about 4–5 kg of Spray-dried Powder) Procedure for $Bi_{1.0}$ Batch
2 Solutions Are Prepared
a) Iron cobalt bismuth nitrate solution (solution A)
   1191.4 g of iron nitrate (14.2% by weight of Fe) are added, while stirring, to 3427.6 g of a cobalt nitrate solution (12.4% by weight of Co) preheated to 60° C. After the end of the addition, stirring is continued for a further 30 minutes, the temperature being kept constant at 60° C. Finally, 1922.5 g of the bismuth nitrate solution (11.2% by weight of Bi) are added. Stirring is again continued for 10 minutes at 60° C.
b) Molybdenum-potassium solution (solution B)
   9.88 g of KOH solution (46.8% by weight of KOH) are added, while stirring, to 2500 g of demineralized water and the mixture is heated to 60° C. while stirring. 2182.9 g of ammonium heptamolybdate are dissolved in this solution at 60° C. while stirring. This solution is stirred for 1 hour, a clear solution being obtained.
Precipitation: Solution A is added in the course of 15 minutes by means of a pump to the initially taken solution B while stirring. At the end of the addition, stirring is continued for at least a further 5 minutes, after which 188.2 g of silica sol (50% by weight of $SiO_2$, density from 1.36 to 1.42 g/ml, pH from 8.5 to 9.5, maximum alkali metal content 0.5% by weight) are added. Stirring is continued for at least 5 minutes. During this time, the temperature of the precipitation batch is kept constant at 60° C.
Spray-drying: This solution is then sprayed in a spray-dryer. The inlet temperature here is 380+/−10° C. and the outlet temperature 115+/−5° C. The chemical composition of the powder thus obtained (4266 g), referred to below as SPLV, is $Mo_{12}Co_7Fe_{2.94}Bi_1Si_{1.52}k_{0.08}O_x$.

As further examples, the following SPLV with varying Bi contents have been prepared:

TABLE 1

Addition of bismuth solution for precipitation batch

| Bi content (or Mo$_{12}$) | Added Bi solution [g] |
|---|---|
| 0 (comparison) | |
| 0.3 | 576.7 |
| 0.45 | 865.1 |
| 0.6 | 1153.5 |
| 0.8 | 1538 |
| 1 | see above |
| 1.5 (comparison) | 2884 |
| 2 (comparison) | 3845 |
| 3 (comparison) | 5767 |

2. Preparation and Testing of the Catalysts

2.1 Preparation and Testing of Catalyst Chips+One-pot Spray Batch a) Kneading: 400 g of the spray-dried powder having the composition Mo$_{12}$Co$_7$Fe$_y$Si$_{1.5}$K$_{0.08}$O$_x$ (y=from 0 to 3) are kneaded in a 2 l kneader after the addition of 45 to 65 ml of water. The kneading is effected in three steps of 5, 10 and 15 minutes. After a kneading time of 5 or 10 minutes, the kneading material is again divided up manually and thoroughly mixed in order to ensure uniform incorporation.

b) Drying: After the kneading, the coarsely divided up kneaded material is dried for 2 hours in a drying oven at 120° C. The kneaded material dried in this manner is brought to a particle size of from 0.71 to 1.6 mm (chips) by mechanical stress and fractional sieving.

c) Decomposition: The decomposition of the committed catalyst chips is effected in a laboratory rotating tube for 2 hours at 250° C. in a stream of nitrogen.

d) Calcination: The calcination is likewise effected in a laboratory rotating tube for 6 hours at from 466 to 471° C. in a stream of air.

The catalyst chips thus obtained are tested as follows:

About 30 g of these chips were installed in a tubular reactor having an internal diameter of 8 mm. Usually, bed heights of about 65 cm are reached in the tube reactor (corresponding to a bulk density of from 0.9 to 0.95 g/ml). At a constant operating temperature of 359° C., the amount of feed gas (mixture of 5% by volume of propene, 9.5% by volume of oxygen and 85.5% by volume of nitrogen) is varied until the propene conversion, measured as $$CON_{Propene}\ [\%] = \frac{C_{Propene,\,inlet} - C_{Propene,\,outlet}}{C_{Propene,\,inlet}} \cdot 100,$$

is 95%. The selectivity with respect to the desired products is acrolein ($S_{ACR}$) and acrylic acid ($S_{ACS}$) is measured. These are calculated as follows:

$$S_{ACR}\ [\%] = \frac{C_{ACR,\,outlet}}{C_{Propene,\,inlet} - C_{Propene,\,outlet}} \cdot 100$$

$$S_{ACA}\ [\%] = \frac{C_{ACA,\,outlet}}{C_{Propene,\,inlet} - C_{Propene,\,outlet}} \cdot 100$$

The selectivity for the desired products ($S_{DP}$) is:

$$S_{DP}\ [\%] = S_{ACA} + S_{ACR}$$

When testing these catalysts, the following values were determined:

TABLE 2

Performance of the catalyst chips

| Con-secutive No. | $T_{Calc.}$ [° C.]/6 h | Bi con-tent | Space velocity$^1$ | Con$_{Propene}$ [%] | $S_{AC}$ [%] | $S_{ACA}$ [%] | $S_{DP}$ [%] |
|---|---|---|---|---|---|---|---|
| V1 | 467 | 0 | 1.74 | 60 | 74.5 | 0 | 74.5 |
| 2 | 471 | 0.3 | 3 | 95 | 90.3 | 6.8 | 97.1 |
| 3 | 469 | 0.6 | 4.9 | 95 | 90.2 | 7.4 | 97.6 |
| 4 | 471 | 1 | 3 | 95 | 89.6 | 4.1 | 93.7 |

$^1$Expressed as $1_{Propene}$ (S.T.P.)/h

2.2 Preparation and Testing of Coated Catalysts, One-pot Spray Batch

In the preparation of the coated catalysts, the procedure is as for the process steps of kneading, drying and decomposition, as described under 2.1. These are followed by the steps below:

a) Milling: The decomposed catalyst precursor is milled to a particle size of $\leq 0.12$ mm in a centrifugal mill (type ZM 100, Retsch).

b) Coating: This powder is applied to steatite beads (nonporous, diameter from 3 to 4 mm) in a manner known per se (cf. for example DE-A 29 09 671 and EP-A 0 293 859). A coating aid is as a rule water or a water/glycerol mixture, but may also be a mixture of water/alcohol and tetramethoxysilane or tetraethoxysilane, for example to obtain particularly abrasion-resistant catalysts. Suitable alcohols are methanol, ethanol, isopropanol, n-butanol and tert-butanol. The coat fraction (C) is calculated as follows:

$$S\ [\%] = 100 - \frac{m_{steatite}}{m_{steatite} + m_{Activecomponent}} \cdot 100$$

c) Calcination: As described under 2.1, for temperature see Table 3.

In the case of these coated catalysts, the testing is likewise carried out in a reactor having an internal diameter of 15 mm. Here, 120 g of catalyst are introduced. The reaction temperature here is varied until propene conversion has reached 95% at a propene space velocity of 5 $1_{Propene}$ (S.T.P.)/h.

TABLE 3

Performance of the coated catalysts

| Consecutive No. | Bi content | $T_{Calc.}$ | S | Space velocity | Temperature | $Con_{Propene}$ | $S_{ACR}$ | $S_{ACA}$ | $S_{DP}$ |
|---|---|---|---|---|---|---|---|---|---|
| 5 | 0.3 | 477 | 50 | 4.9 | 386 | 95.5 | 73.4 | 21.8 | 95.2 |
| 6 | 0.45 | 474 | 51 | 5 | 304 | 95 | 89.5 | 3.9 | 93.4 |
| 7 | 0.6 | 468 | 50 | 5 | 321 | 95.1 | 90.8 | 5.6 | 96.4 |
| 8 | 0.8 | 474 | 50 | 5 | 318 | 95 | 91.6 | 4.3 | 95.9 |
| V9 | 2 | 466 | 50 | 4.7 | 311 | 95.5 | 72.8 | 3.5 | 76.3 |
| V10 | 3 | 473 | 52 | 5 | 313 | 95.2 | 86.2 | 3.4 | 89.6 |

2.3 Preparation and Testing of Catalysts of Separately Prepared Powders

Catalysts which were prepared by mixing two separately prepared powders are described below. The preparation of the novel catalyst powders 1 corresponds to the procedure described above. Before the active material is kneaded, the two powers are homogeneously mixed in the weight ratio stated in the table. Altogether, two different additional catalyst powders (referred to as powder 2 below) are used:

1. $Bi_2W_2O_9$ (ASTM No. 33-0221)

Preparation analogous to U.S. Pat. No. 5,449,821, Example a) having a mean particle diameter of from 1 to 25 μm.

2. $Bi_2Mo_3O_{12}$ (ASTM No. 21-0103)

389.2 g of ammonium heptamolybdate are dissolved in 500 g of demineralized water at 60° C. A bismuth nitrate solution containing 11.2% by weight of bismuth is added to this solution while stirring in the course of 90 minutes. After the end of the addition, the suspension is stirred for a further 30 minutes. The suspension is dried by means of a spray-dryer. The dried powder is decomposed in a laboratory oven at 220° C. in the course of 2 hours. The calcination is effected at 580° C. in the course of 8 hours. The substance thus obtained can be characterized by an X-ray diffraction pattern. This substance has a typical reflection found for this compound in the ASTM index under the number 21-0103.

The table below gives an overview of all catalysts prepared according to this concept. The powder 1 corresponds to the Examples stated further above.

The Testing is effected according to the procedure described further above, i.e. the chips are tested in an 8 mm tube at 358° C. and the coated catalysts are tested at a specified propene space velocity of 5 $l_{propene}$ (S.T.P.)/h in a 15 mm tube.

TABLE 4

Preparation of mixed-phase catalysts

| Consecutive No. | BI content (corres. consecutive No.) | Powder 2 | Mixing ratio [g of powder 1/g of powder 2] | Coat fraction | $T_{Calc.}$ [° C.]/6 h |
|---|---|---|---|---|---|
| 11 | 0.6 (No. 3) | $Bi_2Mo_3O_{12}$ | 500/52 | 50 | 471 |
| 12 | 1.0 (No. 4) | $Bi_2Mo_3O_{12}$ | 550/55.2 | 51 | 473 |
| 13 | 0.6 (No. 3) | $Bi_2Mo_3O_{12}$ | 400/41.7 | Chips | 469 |
| 14 | 0.6 (No. 3) | $Bi_2W_2O_9$ | 400/64.5 | Chips | 467 |
| 15 | 0.3 (No. 2) | $Bi_2W_2O_9$ | 400/66.3 | Chips | 468 |
| 16 | 0.3 (No. 2) | $Bi_2Mo_3O_{12}$ | 400/42.7 | Chips | 478 |

TABLE 5

Performance of the mixed-phase catalysts

| Consecutive No. | Bi content (total) | Velocity[1] | Temp | $Con_{Propene}$ | $S_{ACR}$ | $S_{ACA}$ | $S_{DP}$ |
|---|---|---|---|---|---|---|---|
| 11 | 1.6 | 4.9 | 345 | 94.7 | 87.3 | 9.7 | 97 |
| 12 | 2 | 5.2 | 325 | 95.0 | 91.4 | 4.4 | 95.8 |
| 13 | 1.6 | 2.45 | 359 | 95.0 | 88 | 9.4 | 97.4 |
| 14 | 1.6 | 2.56 | 358 | 95.0 | 87.5 | 9.4 | 96.9 |
| 15 | 1.3 | 3.69 | 359 | 94.9 | 89.4 | 7.5 | 96.9 |
| 16 | 1.3 | 3.35 | 358 | 95.0 | 90.1 | 6.9 | 97 |

2.4 Preparation and Testing of Annular Catalysts in Industrial Tubes

The industrial tubes have a diameter from 21 to 26 mm. The catalysts used in the industrial tubes differ from the materials described so far in that, instead of catalyst chips, an annular catalyst corresponding to a cylinder with the height h and the diameter D, which has a centered round hole with the diameter d, is used. This annular catalyst is prepared in a manner known per se from the spray-dried powder using graphite (from 1 to 3% by weight added) as a pelleting aid. The catalyst rings are characterized by the dimensions of external diameter, pellet height and internal diameter. Usually, pellets having the geometry 5×3×2 or 5×2×2 mm (D×h×d) are used.

The thermal treatment of the catalyst ring is carried out in a plurality of stages, in each case for from 1 to 2 hours at 190, 220 and 245° C. and then for from 4 to 6 hours at the final calcination temperature stated in the table. This catalyst is introduced into a reaction tube having an internal diameter of 26 mm, the bed height of the catalyst being 270 cm. A thermal sleeve of 4 mm diameter is present in the middle of the tube and serves for determining the temperature variation. The filled catalyst volume is 1.4 l and the catalyst mass is 1.4 kg. In these examples, the propene space velocity is stated not in liters (S.T.P.) of propene per hour but in liters (S.T.P.) of propene per liter of catalyst per hour, i.e. in the unit [$h^{-1}$]. These catalysts are operated at a propene conversion from 93 to 95.5%, assuming that they have a corresponding basic activity. The composition of the feed gas is 5.5% y volume of propene, 9.6% by volume of $O_2$, 2.4% by volume of $H_2O$ and 82.5% by volume of $N_2$. The inlet pressure before the catalyst bed is 1.2 bar gage pressure. The maximum temperature reached inside the catalyst bed in the operating state was 418° C. (at a space velocity of 150 $l_{Propene}$ (S.T.P.) per $l_{Catalyst}$ per h). The spent catalyst was regenerated by treatment with a mixture of 95% by volume of $N_2$ and 5% by volume of $O_2$ at 328° C. for 24 hours. In the table below, STY is space-time yield.

The results are summarized in the Table below:

DE-A-2741132 discloses a catalyst which is capable of converting not more than 215 g of propene per l per h under comparable technical conditions (4 m length, 25 mm internal diameter, 2 l of catalyst), the selectivity with respect to the desired products being significantly lower than with the use of the novel catalysts.

DE-A-3114709 discloses, for example in Example 9, a catalyst for propene oxidation which requires a bath temperature as high as 370° C. at a space velocity of 105 $h^{-1}$ and is therefore unsuitable for higher propene space space velocities since, owing to the high temperatures, an unsatisfactorily short life is to be expected here.

3. Characterization of the End Product 3.1 Porosimetry (Chips)

| | |
|---|---|
| Pore volume (from mercury porosimetry) | 0.3–0.35 ml/g |
| BET surface area (from $N_2$ sorption) | 5–8 $m^2/g$ |

TABLE 6

Performance of the catalysts in the industrial tube

| Consecutive No. | Bi content | $T_{Calc.}$ | Space velocity[1] | Temperature (salt bath) | $Con_{Propene}$ [%] | $S_{ACR}$ [%] | $S_{ACA}$ [%] | $S_{DP}$ [%] | $STY^2$ |
|---|---|---|---|---|---|---|---|---|---|
| 1 | 0 | 467 | 100 | 350 | 75.2 | 82.0 | 1.2 | 83.2 | 117.5 |
| 3 | 0.6 | 469 | 125 | 318 | 93.4 | 92.5 | 4.6 | 97.1 | 212.9 |
| 3[3] | 0.6 | 469 | 125 | 328 | 94.0 | 93.0 | 4.4 | 97.4 | 215.0 |
| 3[4] | 0.6 | 469 | 125 | 318 | 94.0 | 92.0 | 4.8 | 96.8 | 213.6 |
| 3 | 0.6 | 469 | 150 | 329 | 93.5 | 90.2 | 6.7 | 96.9 | 255.3 |
| 4 | 1 | 471 | 125 | 325 | 94.0 | 90.2 | 4.4 | 94.6 | 208.8 |
| 4[3] | 1 | 471 | 125 | 338 | 94.2 | 89.0 | 5.2 | 94.2 | 208.3 |
| 9 | 1.5 | 470 | 125 | 320 | 95.2 | 89.3 | 3.8 | 93.1 | 208.1 |

[1]$l_{Propene}$ (S.T.P.) per $l_{Catalyst}$ per h
[2]Calculated as $g_{Converted\ propene}$ per $l_{Catalyst}$ per h, the amount converted to ACR and ACA being taken into account
[3]After an operating time of 2000 h
[4]After treatment with a mixture of 95% by volume of $N_2$ and 5% by volume of $O_2$ at 328° C. for 24 hours Deactivation of the catalyst during the use of the catalysts is reversible, i.e. a thermal treatment—as described above—at reaction temperature in air or nitrogen or a mixture of the two for 24 hours restores the original activity/selectivity.

Comparative Experiment

Catalysts F2 and F3 according to EP-A-0 575 897 are tested in an industrial tube analogously to the description 2.4 above.

3.2 Analyses of the Coated Catalysts

| | |
|---|---|
| Pore volume (from mercury porosimetry) | 0.2–0.3 ml/g |
| BET surface area (from $N_2$ sorption) | 7–13 $m^2/g$ |

TABLE 7

| Comp. Example | Space velocity[1] | Temp. (salt bath) | $Con_{Propene}$ [%] | $S_{ACR}$ [%] | $S_{ACA}$ [%] | $S_{DP}$ [%] | $STY^2$ |
|---|---|---|---|---|---|---|---|
| F2 from EP 575 897 | 100 | 345 | 94.1 | 88.0 | 7.5 | 95.5 | 169 |
| F3 from EP 575 897 | 100 | 334 | 95.0 | 89.4 | 5.9 | 95.3 | 170 |

[1]$l_{Propene}$ (S.T.P.) per $l_{Catalyst}$ per h
[2]Calculated as $g_{Converted\ propene}$ per $l_{Catalyst}$ per h, the amount converted to ACR and ACA being taken into account The comparison shows that the novel catalysts are considerably superior to the comparative catalyst with respect to the achievable space-time yield.

3.3 Phase Composition

In the prepared catalyst, the following solid phases can be detected by means of X-ray diffractometry:

TABLE 8

Phases characterizable in the X-ray diffraction pattern, as a function of the composition of the spray-drying powder

| Bi content | β-CoMoO$_4$ 210868 | Fe$_2$(MoO$_4$)$_3$ 310642 | MoO$_3$ 5-0508 | β-CoMoO$_4$ 251434 | Bi$_2$Mo$_3$O$_{12}$ 210103 | Co$_6$Mo$_{12}$Fe$_4$Bi$_{1.5}$O$_x$ 370974 | Bi$_3$FeMo$_2$O$_{12}$ 270047 |
|---|---|---|---|---|---|---|---|
| 0 | + | + | + | + | − | − | − |
| 0.3 | + | + | − | + | + | − | − |
| 0.45 | + | + | − | − | − | + | − |
| 0.6 | + | + | − | + | + | + | − |
| 0.8 | + | + | − | − | − | + | − |
| 1 | + | + | − | + | + | + | − |
| 2 | + | + | − | − | − | − | + |
| 3 | + | + | − | − | − | − | + |

The second line in the table indicates the ASTM numbers. The following are found:

1. β-CoMoO$_4$ as main component of the catalyst. Fe$_2$(MoO$_4$)$_3$ as most important secondary component.
2. Exclusion of MoO$_3$ as soon as Bi has been added.
3. Formation of the compounds Bi$_2$Mo$_3$O$_{12}$ and Co$_6$Mo$_{12}$Fe$_4$Bi$_{1.5}$O$_x$ in the range (Mo$_{12}$Bi$_{0.3}$ to Mo$_{12}$Bi$_{1.0}$) of the Bi addition (a more exact differentiation between the two compounds is difficult owing to many line superpositions with different phases).
4. Formation of a phase (Bi$_3$FeMo$_2$O$_{12}$) which is undesired because it is unselective, when larger amounts of Bi are added (Mo$_{12}$Bi$_2$ and Mo$_{12}$Bi$_3$).

We claim:

1. A multimetal oxide material containing crystalline fractions consisting essentially of $$Mo_{12}Bi_aX^1_bFe_cX^2_dX^3_eO_y \quad (I)$$

where:

X$^1$ is Co and/or Ni,
X$^2$ is Si and/or Al,
X$^3$ is an alkali metal,
0.45≦a≦1,
2≦b≦10,
0.5≦c≦10,
0≦d≦10,
0≦e≦0.5 and
y is the number of oxygen atoms required for charge neutrality of the multimetal oxide material, the crystalline fractions comprising β-X$^1$MoO$_4$ as the main crystalline fraction component, and Fe$_2$(MoO$_4$)$_3$ and X$^1_6$Mo$_{,12}$Fe$_4$Bi$_{1.5}$O$_x$ as secondary crystalline fraction components and wherein x has the same meaning as y, and no MoO$_3$ as a crystalline fraction.

2. A multimetal oxide material as claimed in claim 1, wherein no Bi$_3$FeMo$_2$O$_{12}$ is present in the crystalline fractions.

3. A multimetal oxide material as claimed in claim 1, wherein X$^1$ is Co.

4. A process for the preparation of a multimetal oxide material as claimed in claim 1, in which a) a first aqueous solution A of the constituents Bi, Fe and X$^1$ is prepared,
b) a second aqueous solution B of the constituents Mo and X$^3$ is prepared,
c) the solutions A and B are mixed, a solution or suspension of the constituent X$^2$ being mixed with the solution A, B or a mixture thereof,
d) removing the liquid component of the mixed solutions or suspension and obtaining a solid material which is dried, and
e) the product obtained in d) is calcined at a temperature ranging from 465 to 477° C.

5. A process as claimed in claim 4, wherein the calcination is conducted at from 465 to 474° C.

6. The process as claimed in claim 4, wherein the drying of step (d) is spray drying.

7. The process as claimed in claim 6, wherein spray drying is conducted in a spray tower having an inlet which is at a temperature of about 400° C. and an outlet at a temperature ranging from 120 to 140° C.

8. A method for the gas phase oxidation of an organic compound, comprising:

oxidizing the organic compound in the gas phase in the presence of the multimetal oxide material of claim 1 as a catalyst.

9. The method as claimed in claim 8, for the selective gas-phase oxidation of alkenes.

10. The method as claimed in claim 9, for the preparation of α,β-unsaturated aldehydes and/or carboxylic acids.

11. A catalyst comprising:

the multimetal oxide material as claimed in claim 1 in the form of chips, moldings or as a coating on a substrate material.

12. A catalyst as claimed in claim 11, which additionally comprises at least one bismuth-containing oxide.

13. A multimetal oxide material as claimed in claim 1, wherein Bi$_2$Mo$_3$O$_{12}$ is present as an additional secondary component in the crystalline fractions of the multimetal oxide material.

* * * * *